United States Patent [19]

Beedle et al.

[11] Patent Number: 4,642,379

[45] Date of Patent: Feb. 10, 1987

[54] INTERMEDIATES FOR ANTICONVULSANT AGENTS

[75] Inventors: Edward E. Beedle, Indianapolis; David W. Robertson, Greenwood, both of Ind.

[73] Assignee: Eli Lilly and Company, Ind.

[21] Appl. No.: 771,455

[22] Filed: Aug. 30, 1985

[51] Int. Cl.$^4$ .................................. C07D 103/76
[52] U.S. Cl. ....................... 564/155; 564/157; 540/610; 546/234; 544/165; 544/400; 548/568
[58] Field of Search ........................ 564/155

[56] References Cited

U.S. PATENT DOCUMENTS 4,004,029  1/1977  Collins ............................. 424/325
4,379,165  4/1983  Clark ............................... 424/324
4,629,740  4/1984  Robertson.

OTHER PUBLICATIONS

Grammaticakis, *Compt. Rend.*, 259(23), 4295 (1964) (English Abstract Chemical Abstracts 62:11732b (1965)).
Thiele, Chemical Abstracts 75:35466g (1971).
Thiele, Chemical Abstracts 73:87659a (1970).
Chemical Abstracts 76:140260d (1972).
Dimroth et al., Chemical Abstracts 83:12187t (1975).
Moffett et al., *J. Med. Chem.*, 14(10), 963 (1971).

*Primary Examiner*—Norma S. Milestone
*Attorney, Agent, or Firm*—Charles W. Ashbrook; Robert A. Conrad

[57] ABSTRACT

This invention provides certain 4-acylamino benzamide derivatives, their pharmaceutical formulations, and their use as anticonvulsant agents.

5 Claims, No Drawings

INTERMEDIATES FOR ANTICONVULSANT AGENTS

BACKGROUND OF THE INVENTION

The several anticonvulsant drugs marketed in the United States provide significant seizure relief for only 50–75% of epileptic patients. The therapeutic effects are sometimes accompanied by serious side effects such as sedation, ataxia, psychoses, suicidal depression, gastrointestinal disturbances, gingival hyperplasia, lymphadenopathies, megaloblastic anemias, hepatotoxicity, nephropathies, hirsutism, and fetal malformations. These side effects, which range in severity from mild sedation to death from aplastic anemia, are particularly troublesome since most of the marketed anticonvulsants have very low therapeutic ratios. For example, phenytoin, one of the most widely used anticonvulsants, controls seizures in man only when plasma levels reach 10 mcg/ml. Toxic effects such as nystagmus are seen at around 20 mcg/ml, ataxia is obvious at 30 mcg/ml, and lethargy is apparent at about 40 mcg/ml. See "The Pharmacological Basis of Therapeutics" (Gilman, Goodman, and Gilman, ed., 6th Ed., MacMillan Publishing Co., Inc., New York, N.Y. (1980)), p. 455, In view of these facts, most epileptologists indicate there is a definite need for more selective and less toxic anticonvulsant drugs.

SUMMARY OF THE INVENTION

This invention provides p-acylaminobenzamides of the formula I

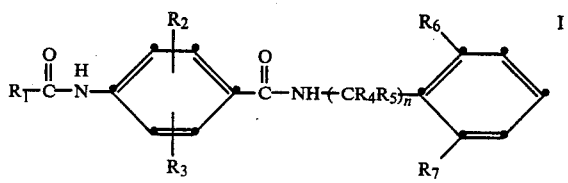

wherein $R_1$ is $C_1$–$C_6$ alkyl, $C_3$–$C_7$ cycloalkyl, or $R_8R_9N$—alk—, where $R_8$ and $R_9$ are each independently hydrogen, $C_1$–$C_6$ alkyl, or $C_3$–$C_7$ cycloalkyl, or when taken together with the nitrogen atom to which they are attached $R_8$ and $R_9$ are pyrrolidino, piperidino, homopiperidino, morpholino, or N-methylpiperazino, and "alk" is a divalent organic radical derived from a $C_1$–$C_6$ aliphatic hydrocarbon, $R_2$, $R_3$, $R_4$, $R_5$, $R_6$, and $R_7$ are each independently hydrogen or methyl; and n is 0 or 1; and pharmaceutically acceptable acid addition salts thereof.

This invention also provides a method for treating and preventing convulsions in mammals in need of such treatment which comprises administering to said mammal an effective amount of a compound as defined above.

According to a further aspect of the present invention, there are provided pharmaceutical formulations which comprise an active ingredient a benzamide of formula I in association with a pharmaceutically acceptable carrier or diluent.

This invention also provides compounds of the formula II

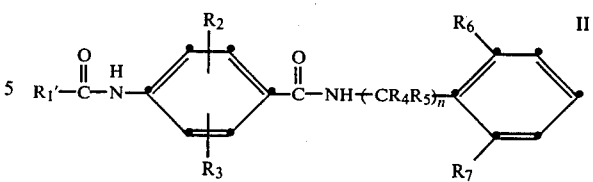

wherein $R_2$, $R_3$, $R_4$, $R_5$, $R_6$, $R_7$, and n are the same as previously defined, and $R_1'$ is bromo- or chloro-substituted $C_1$–$C_6$ alkyl. These halo-acyl derivatives are useful as intermediates for preparing some of the anticonvulsant p-acylaminobenzamides of formula I.

DETAILED DESCRIPTION AND PREFERRED EMBODIMENT

The present invention relates to organic compounds that are useful for treating and preventing convulsions in mammals.

The term "$C_1$–$C_6$ alkyl" refers to straight and branched aliphatic residues of one to six carbon atoms such as methyl, ethyl, propyl, isopropyl, t-butyl, hexyl, and the like. The term "alk" refers to a divalent organic radical derived from a $C_1$–$C_6$ straight or branched aliphatic hydrocarbon such as —$C_2$—, —$CH(CH_3)$—, —$C(CH_3)_2$—, —$CH(C_2H_5)$—, —$CH_2CH_2$—, —$CH(CH_3)CH_2$—, —$CH_2CH(CH_3)$—, —$CH_2CH_2CH_2$—, —$CH_2CH_2CH_2CH_2CH_2CH_2$—, and the like.

The term "$C_3$–$C_7$ cycloalkyl" refers to the saturated alicyclic rings of three to seven carbon atoms such as cyclopropyl, methylcyclopropyl, cyclobutyl, cyclopentyl, cyclohexyl, 1-, 2-, 3-, or 4-methylcyclohexyl, cycloheptyl, and the like.

The preferred compounds of this invention are those wherein n is 0, $R_2$ and $R_3$ are each hydrogen, and at least one and preferably both of $R_6$ and $R_7$ are methyl. Alternatively, when n is 1, it is preferred that at least one of $R_4$ and $R_5$ methyl and that $R_6$ and $R_7$ are each hydrogen. $R_1$ is preferably $R_8R_9N$—alk—where neither $R_8$ nor $R_9$ is hydrogen and "alk" is methylene.

The pharmaceutically acceptable acid addition salts of this invention can be prepared by standard methods known in the art employing those acids of sufficient acidity to form acid addition salts of those compounds wherein $R_1$ is $R_8R_9N$—alk—. These include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxy-alkanoic and -alkanedioic acids, aromatic acids, aliphatic and aromatic sulfonic acids, etc. Such pharmaceutically acceptable salts thus include sulfate, metaphosphate, pyrophosphate, chloride, bromide, iodide, fluoride, oxalate, maleate, benzenesulfonate, toluenesulfonate, chlorobenzenesulfonate, methanesulfonate, propanesulfonate, naphthalene-1-sulfonate, naphthalene-2-sulfonate and the like. The Preferred salts are those derived from inorganic acids, especially hydrochloric acid.

Certain of the compounds of formula I and II can be prepared by standard acylation procedures well known in the art as summarized by the following scheme:

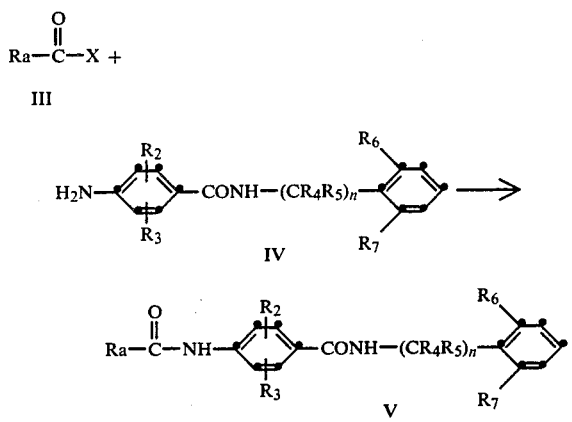

wherein Ra is $C_1$–$C_6$ alkyl or bromo- or chloro-substituted $C_1$–$C_6$ alkyl, and X is bromo, chloro, —OH, or —OCORa.

Although any of a number of general acylation techniques may be employed, it is preferred that an acid halide or anhydride (III) and the aniline (IV) be reacted in a non-reactive solvent, such as tetrahydrofuran or dimethylformamide, preferably in the presence of an acid scavenger such as a carbonate, especially potassium carbonate, or an organic base, such as triethylamine or pyridine. Although it is preferred that the reactants be added in the approximate molar ratio of about 1.25:1 (III:IV), other ratios are operative. The reaction is carried out from about room temperature up to the reflux temperature of the reaction mixture. Under the preferred conditions of approximately 25° C., the reaction is generally complete in 1–2 hours.

Standard coupling techniques employing carboxylic acids (III, X=—OH) may also be employed using coupling reagents such as DCC, EEDQ, CDI, etc.

The aminoacyl substituted compounds of this invention may be prepared from the corresponding halo acylated compounds by reacting compound V (Ra is bromo- or chloro-substituted $C_1$–$C_6$ alkyl) with an amine of the formula $R_8R_9NH$. In general, this reaction is accomplished by reacting a large excess of the amine with the halo intermediate, preferably in the presence of a non-reactive solvent such as tetrahydrofuran. In the case of water-miscible solvents, water may also be employed as a cosolvent. The reaction is generally carried out at temperatures from about 20° C. up to the reflux temperature of the reaction mixture. At the preferred reaction temperature of 20°–30° C., the reaction is generally complete within approximately 12 hours.

The intermediates of Formulas III and IV and other necessary reagents are commercially available, are known in the art, or can be prepared by methods taught in the literature. In particular, the compounds of Formula IV can be prepared according to methods described in U.S. Pat. No. 4,379,165.

The p-acylaminobenzamides of this invention are anticonvulsant agents and may be administered by various routes including the oral, rectal, transdermal, subcutaneous, intravenous, intramuscular, or intranasal routes, being usually employed in the form of a pharmaceutical composition. It is a special feature of these compounds that they are effective following oral administration. The invention includes a pharmaceutical composition comprising from about 1% to about 95% by weight of a p-aminobenzamide of Formula I, or a pharmaceutically acceptable acid addition salt thereof, associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 5 to 500 mg, more usually 25 to 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg/kg of body weight. In the treatment of adult humans, the range of about 1 to 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

The following examples further illustrate the preparation of the intermediates, compounds, and formulations of this invention. The examples are illustrative only and are not intended to limit the scope of the invention in any way.

EXAMPLE 1

4-(Acetylamino)-N-(2,6-dimethylphenyl)benzamide

To a solution of 2.0 g of 4-amino-N-(2,6-dimethylphenyl)benzamide in dimethylformamide were added 1 ml of pyridine followed by 710 μl of acetyl chloride. The reaction was stirrred at room temperature for 2 hours, diluted with water, and chilled to approximately 4° C. The title product was recovered by filtration in 85% yield, m.p. 293°–295° C.

Analysis for $C_{17}H_{18}N_2O_2$: Calculated: C, 72.32; H, 6.43; N, 9.92; Found: C, 72.12; H, 6.19; N, 9.70.

EXAMPLES 2-11

The following compounds were prepared according to the general procedure of Example 1 employing the appropriate 4-aminobenzamide derivative and the corresponding acid chloride.

2. N-(2,6-dimethylphenyl)-4-[(1-oxopropyl)amino]benzamide, 84% yield, m.p. 285°-286° C.

Analysis for $C_{18}H_{20}N_2O_2$: Calculated: C, 72.95; H, 6.80; N, 9.45; Found: C, 72.70; H, 6.57; N, 9.15.

3. N-(2,6-dimethylphenyl)-4-[(2-methyl-1-oxopropyl)amino]benzamide, 73% yield, m.p. 283°-284° C.

Analysis for $C_{17}H_{22}N_2O_2$: Calculated: C, 73.52; H, 7.14; N, 9.03; Found: C, 73.57; H, 7.15; N, 8.82.

4. (S)-4-(acetylamino)-N-(1-phenylethyl)benzamide, 88% yield, m.p. 225°-226° C.

Analysis for $C_{17}H_{18}N_2O_2$: Calculated: C, 72.32; H, 6.43; N, 9.92; Found: C, 72.33; H, 6.57; N, 9.86.

5. (R)-4-(acetylamino)-N-(4-phenylethyl)benzamide, 88% yield, m.p. 225°-226° C.

Analysis for $C_{17}H_{18}N_2O_2$: Calculated: C, 72.32; H, 6.43; N, 9.92; Found: C, 72.08; H, 6.20; N, 9.68. 6. 4-(Acetylamino)-N-(1-phenylethyl)benzamide, 94% yield, m.p. 227°-228.5° C.

Analysis for $C_{17}H_{18}N_2O_2$: Calculated: C, 72.32; H, 6.43; N, 9.92; Found: C, 72.85; H, 6.30; N, 9.62.

7. 4-[(Chloroacetyl)amino]-N-(2,6-dimethylphenyl)benzamide, 92% yield, m.p. 246°-248° C.

Analysis for $C_{17}H_{17}ClN_2O_2$: Calculated: C, 64.46, H, 5.41; N, 8.84; Found: C, 64.68; H, 5.48; N, 9.01.

8. 4-[(3-Chloro-1-oxopropyl)amino]-N-(2,6-dimethylphenyl)benzamide, 88% yield, m.p. 254° C.

Analysis for $C_{18}H_{19}ClN_2O_2$: Calculated: C, 65.35; H, 5.79; N, 8.47; Found: C, 65.43; H, 5.89; N, 8.30.

9. 4-[(2-Chloro-1-oxopropyl)amino]-N-(2,6-dimethylphenyl)benzamide, 91% yield, m.p. 269°-270° C.

Analysis for $C_{18}H_{19}ClN_2O_2$: Calculated: C, 65.35; H, 5.79; N, 8.47; Found: C, 65.37; H, 5.75; N, 8.66.

10. 4-[(4-Chloro-1-oxobutyl)amino]-N-(2,6-dimethyphenyl)benzamide, 88% yield, m.p. 258°-259° C.

Analysis for $C_{19}H_{21}ClN_2O_2$: Calculated: C, 66.18; H, 6.14; N, 8.12; Found: C, 66.12; H, 5.90; N, 7.87.

11. 4-(Acetylamino)-N-(2,6-dimethylphenyl)-3-methylbenzamide, 82% yield, m.p. 273°-275° C.

Analysis for $C_{18}H_{20}N_2O_2$: Calculated: C, 72.95; H, 6.80; N, 9.45; Found: C, 72.96; H, 6.58; N, 9.17.

EXAMPLE 12

4-([(Dimethylamino)acetyl]amino)-N-(2,6-dimethylphenyl)benzamide

A mixture of 3.0 g of 4-[(chloroacetyl)amino]-N-(2,6-dimethylphenyl)benzamide and 22 ml of 40% aqueous dimethylamine in tetrahydrofuran was stirred at room temperature overnight. After the reaction was evaporated to dryness, the residue was taken up in chloroform, washed with 10% aqueous sodium carbonate, water, and a saturated sodium chloride solution, dried over sodium sulfate, and evaporated to dryness. Crystallization from methanol/water provided 2.8 g of the desired title product, m.p. 276°-278° C.

Analysis for $C_{19}H_{23}N_3O_2$: Calculated: C, 70.13; H, 7.12; N, 12.91; Found: C, 70.40; H, 7.10; N, 12.63.

EXAMPLE 13-23

The following products were prepared from the corresponding chloro intermediates and the appropriate amines according to the general procedure of Example 12.

13. N-(2,6-dimethylphenyl)-4-([(methylamino)acetyl]amino)benzamide ethanedioate, 8% yield, m.p. 257°-258° C.

Analysis for $C_{18}H_{21}N_3O_2.C_2H_2O_4$: Calculated: C, 59.84; H, 5.78; N, 10.47; Found: C, 59.61; H, 5.79; N, 10.26.

14. 4-([(Diethylamino)acetyl]amino)-N-(2,6-dimethylphenyl)benzamide ethanedioate, 58% yield, m.p. 205°-206° C.

Analysis for $C_{20}H_{27}N_3O_2.C_2H_2O_4$: Calculated: C, 62.29; H, 6.59; N, 9.47; Found: C, 62.24; H, 6.64; N, 9.14.

15. N-[4-([(2,6-Dimethylphenyl)amino]carbonyl)phenyl]-1-piperidineacetamide, 83% yield, m.p. 215°-217° C.

Analysis for $C_{22}H_{27}N_3O_2$: Calculated: C, 72.30; H, 7.45; N, 11.50; Found: C, 72.42; H, 7.45; N, 11.32.

16. N-[4-([(2,6-Dimethylphenyl)amino]carbonyl)phenyl]-1-pyrrolidineacetamide, 85% yield, m.p. 254°-257° C.

Analysis for $C_{21}H_{25}N_3O_2$: Calculated: C, 71.77; H, 7.17; N, 11.96; Found: C, 71.52; H, 7.09; N, 11.69.

17. N-[4-([(2,6-Dimethylphenyl)amino]carbonyl)phenyl]-4-methyl-1-piperazineacetamide, 53% yield, m.p. 190°-191° C.

Analysis for $C_{22}H_{28}N_4O_2$: Calculated: C, 69.45; H, 7.42; N, 14.73; Found: C, 69.41; H, 7.46; N, 14.50.

18. N-[4-([(2,6-Dimethylphenyl)amino]carbonyl)phenyl]-4-morpholineacetamide, 83% yield, m.p. 201°-203° C.

Analysis for $C_{21}H_{25}N_3O_3$: Calculated: C, 68.64; H, 6.86; N, 11.44; Found: C, 68.66; H, 6.83; N, 11.18.

19. N-[4-([(2,6-Dimethylphenyl)amino]carbonyl)phenyl]-1-pyrrolidinepropanamide, 83% yield, m.p. 180° C.

Analysis for $C_{22}H_{27}N_3O_2$: Calculated: C, 72.30; H, 7.45; N, 11.50; Found: C, 72.17; H, 7.23; N, 11.25.

20. N-[(4-([(2,6-Dimethylphenyl)amino]carbonyl)phenyl]-α-methyl-1-pyrrolidineacetamide, 77% yield, m.p. 218°-220° C.

Analysis for $C_{22}H_{27}N_3O_2$: Calculated: C, 72.30; H, 7.45; N, 11.50; Found: C, 72.50; H, 7.26; N, 11.44.

21. N-[4-([(2,6-Dimethylphenyl)amino]carbonyl)phenyl]hexahydro-1-H-azepine-1-acetamide, 81% yield, m.p. 207°-208° C.

Analysis for $C_{23}H_{29}N_3O_2$: Calculated: C. 72.79; H, 7.70; N, 11.07; Found: C, 72.68; H, 7.50; N, 10.88.

22. 4-([(Ethylamino)acetyl]amino)-N-(1-phenylethyl)benzamide hydrochloride, 61% yield, m.p. 207°-210° C.

Analysis for $C_{19}H_{23}N_3O_2.HCl$: Calculated: C, 63.24; H, 6.42; N, 11.64; Found: C, 63.23; H, 6.17; N, 11.50.

23. N-(2,6-Dimethylphenyl)-4-([(ethylamino)acetyl]amino)benzamide, 58% yield, m.p. 203°-204° C.

Analysis for $C_{19}H_{23}N_3O_2$: Calculated: C, 70.13; H, 7.12; N, 12.91; Found: C, 70.25; H, 7.36; N, 13.00.

The following formulation examples may employ as active compounds any of the pharmaceutical compounds of the invention or their pharmaceutically acceptable salts.

EXAMPLE 24

Hard gelatin capsules are prepared using the following ingredients:

|  | Quantity (mg/capsule) |
|---|---|
| 4-([(Diethylamino)acetyl]-amino)-N—(2,6-dimethylphenyl)benzamide | 250 |
| Starch dried | 200 |
| Magnesium stearate | 10 |

The above ingredients are mixed and filled into hard gelatin capsules in 460 mg. quantities.

EXAMPLE 25

A tablet formula is prepared using the ingredients below:

|  | Quantity (mg/tablet) |
|---|---|
| 4-(Acetylamino)-N—(2,6-dimethylphenyl)benzamide | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 26

An aerosol solution is prepared containing the following components:

|  | Weight % |
|---|---|
| N—(2-methylphenyl)-4-[(2-methyl-1-oxopropyl)amino]benzamide | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 27

Tablets each containing 60 mg of active ingredient are made up as follows:

| (R)-4-(Acetylamino)-N—(1-phenylethyl)benzamide | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 28

Capsules each containing 80 mg of medicament are made as follows:

| 4-([(ethylamino)acetyl]amino)-N—(α,α,2,6-tetramethylbenzyl)benzamide sulfate | 80 mg |
|---|---|
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 29

Suppositories each containing 225 mg of active ingredient are made as follows:

| N—[4-([(2,6-dimethylphenyl)amino]carbonyl)phenyl]-4-methyl-1-piperazineacetamide | 225 mg |
|---|---|
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 30

Suspensions each containing 50 mg of medicament per 5 ml dose are made as follows:

| 4-([(Dimethylamino)acetyl]amino)-N—(2,6-dimethylphenyl)benzamide ethanedioate | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

The compounds of Formula I are anticonvulsant agents with a high therapeutic ratio and long half-life and are therefore useful in the treatment and prevention of convulsions in mammals. Moreover, the anticonvulsant compounds of this invention, in contrast to anticonvulsant benzamides taught in the art, do not cause hemolysis. The compounds are effective against tonic extensor seizures elicited by maximal electroshock and should therefore be useful for treating generalized tonic-clonic ("grand mal"), cortical focal, complex partial (temporal lobe epilepsy), simple partial (focal motor), and post-traumatic seizures in humans. This activity is demonstrated in the electroshock induced convulsion inhibition assay which follows.

In the elctroshock induced convulsion inhibition assay (E.S.), the compound to be tested was suspended in acacia and administered by gavage to each of ten Cox standard strain albino male mice (18-24 g) at the dose level being investigated. Thirty to 180 minutes after compound administration, the mice were subjected to a 0.1 second, 50 milliampere electroshock through corneal electrodes. The animals were examined and evaluated immediately after the electroshock for the occurrence of clonic, flexor tonic, or extensor tonic convulsions, or death and the $ED_{50}$ was determined for each compound as the dose which inhibited the occurrence of extensor tonic convulsions in one half of the animals immediately after the electroshock. For comparison, 18 milliamperes was usually sufficient to produce extensor tonic convulsions in about half of the control animals; at 50 milliamperes, almost all control animals (receiving vehicle only) died. The test results summarized in Table I are reported as the $ED_{50}$ values at the time interval found to provide an optimal response after dosing.

TABLE I

| Anti-convulsant Activity of compounds of Formula I | | |
|---|---|---|
| Example No. | Electroshock $ED_{50}$ (mg/kg)* | Time After dosing (minutes)** |
| 1 | 3.6 | 120 |
| 2 | 10.5 | 60 |
| 3 | 8.2 | 120 |
| 4 | 22.2 | 60 |
| 5 | ca. 100 | 60 |
| 6 | 54 | 180 |
| 11 | 4.5 | 60 |
| 12 | 8.0 | 30 |
| 13 | 6.3 | 120 |

TABLE I-continued

| Anti-convulsant Activity of compounds of Formula I | | |
|---|---|---|
| Example No. | Electroshock $ED_{50}$ (mg/kg)* | Time After dosing (minutes)** |
| 14 | 3.6 | 60 |
| 15 | 9.5 | 60 |
| 16 | 3.75 | 120 |
| 17 | >112 | 30 |
| 18 | 17.5 | 180 |
| 19 | 26.9 | 180 |
| 20 | 42.5 | 180 |
| 21 | 5.1 | 120 |
| 22 | 28 | 60 |
| 23 | 3.2 | 60 |

*oral dose (gavage)-See text for methodology.
**Time (between dosing and administration of the electroshock) providing an optimal response.

We claim:
1. A compound of the formula

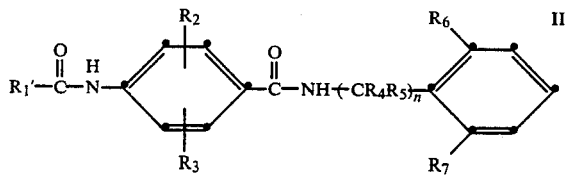

wherein $R_1'$ is bromo- or chloro-substituted $C_1$–$C_6$ alkyl;
$R_2$, $R_3$, $R_4$, $R_5$, $R_6$, and $R_7$ are each independently hydrogen or methyl; and
n is 0 or 1.

2. A compound according to claim 1 wherein n is 0.
3. A compound according to claim 2 wherein $R_6$ and $R_7$ are each methyl.
4. The compound of claim 3 which is 4-[(chloroacetyl)amino]-N-(2,6-dimethylphenyl)benzamide.
5. The compound of claim 3 which is 4-[(3-chloro-1-oxopropyl)amino]-N-(2,6-dimethylphenyl)benzamide.

* * * * *